United States Patent [19]

Kochinke

[11] Patent Number: 5,350,581
[45] Date of Patent: Sep. 27, 1994

[54] METHOD FOR MANUFACTURING TRANSDERMAL DEVICES

[75] Inventor: Frank Kochinke, Fremont, Calif.

[73] Assignee: Pharmetrix Corporation, Menlo Park, Calif.

[21] Appl. No.: 450,409

[22] Filed: Dec. 14, 1989

[51] Int. Cl.⁵ ............................................. A61F 13/00
[52] U.S. Cl. .................................... 424/443; 424/448; 424/449
[58] Field of Search ..................... 424/448, 449, 443

[56] References Cited

U.S. PATENT DOCUMENTS 4,552,751 11/1985 Inaba ...................................... 424/19
4,769,028 9/1988 Hoffman ............................... 424/443
4,844,903 7/1989 Seth ...................................... 424/448

Primary Examiner—Thurman K. Page
Assistant Examiner—D. Gabrielle Phelan
Attorney, Agent, or Firm—Anthony J. Castro

[57] ABSTRACT

A method for fabrication of multilayer transdermal drug release devices that divides the assembly of the various drug delivery components of the device into their unit operations; treats the prefabricated units as modules that are later combined to obtain the finished transdermal drug delivery device. A variety of different configurations are available depending upon the drug or drugs to be administered.

30 Claims, 6 Drawing Sheets 5,350,581

METHOD FOR MANUFACTURING TRANSDERMAL DEVICES

FIELD OF THE INVENTION

This invention is directed to a method for the fabrication of transdermal drug delivery devices.

BACKGROUND OF THE INVENTION

Transdermal drug delivery devices began as simple contrivances that contained a small amount of medicament in an adhesive plaster or patch that was attached to the host organism and simply allowed the drug to migrate from the zone of drug containment in the patch to the skin surface where, under favorable conditions, it passed through the stratum corneum layer of the skin and was absorbed by the host. If the drug was sufficiently skin permeable, the patch size could be adjusted so that the amount of drug entering the system appropriate for the treatment was safe and efficacious. An example of a basic device of this type is found in U.S. Pat. No. 3,598,122. There, the ultimate device was prepared in a series of steps. First, megesterol acetate was deposited upon a sheet of silicone rubber followed by, folding the rubber to enclose the drug, sealing the edges of the rubber, followed by coating one side with an adhesive and the other side with an impermeable cellophane backing. When attached to the host, the drug migrated through the silicone rubber, adhesive and was absorbed by the host. As the difficulties inherent in transdermal absorption drug became known, transdermal drug delivery devices became more complicated. In order to facilitate drug transport through the stratum corneum, skin permeation modifiers (enhancers) were added to patch design to alter the permeability of the skin. Enhancer systems can be combined with the drug as is the transdermal device fabricated in U.S. Pat. No. 3,598,122 or incorporated in the adhesive layer as described in U.S. Pat. No. 4,690,683. In all cases of device fabrication thus far described, except U.S. Pat. No. 4,839,174 and copending application Ser. No. 264,397, now U.S. Pat. No. 4,943,435 by the inventor and incorporated herein by reference, construction of the transdermal devices were accomplished by a series of coating and laminating steps or thermal sealing methods. U.S. Pat. No. 4,556,441 describes a machine for manufacturing transdermal devices via a continuous method. The invention described in U.S. Pat. No. 4,556,441, as in most methods, is relatively inflexible and does not easily permit changes during the fabrication to produce a variety of devices with different therapeutic characteristics. Application of multiple coatings (the most common method for the fabrication of transdermal drug delivery devices) has several problems associated with this technique for device assembly. For example, coating of chemically dissimilar materials typically leads to delamination problems due to poor adhesion between the dissimilar layers. In many cases, drug matrices and adhesives are deposited by coating solvent based solutions. If solvent residues are not completely removed from the first applied coating before the next layer is applied, solvent from the first will be effectively trapped between layers. Residual solvent can interact with various components of the device and over time, seriously affect the efficacy and safety of the device. Consequently, deposition of the initial layer and additional layers must be timed to the removal of carriers for the adhesive, drug, enhancer, and the like. In another technique. U.S. Pat. No. 4,695,277, a layered device may be assembled and then sealed by vacuum forming or under some favorable situations, heat sealing without vacuum. The dangers in these techniques lie in the dangerous consequences of inadequate temperature control which would lead to poor seals if the temperature is too low and degradation of the drug and other components if it is too high. In the case of reservoir devices, liquid or gelled drugs must be accurately deposited into cavities formed during a vacuum forming process. Additionally, volatile drugs can be lost during the vacuum forming process resulting in inconsistent drug levels and concomitant unreliable performance of the device. Since the device is completed upon sealing, one cannot compensate for inadequate drug levels but must discard the out of specification product. Thus, it will be appreciated that previously described methods for fabrication of transdermal delivery devices lack versatility and are not conducted as unit operations.

DESCRIPTION OF THE INVENTION

Transdermal delivery devices have many common indispensable elements because they attempt to achieve a common goal through a common means, i.e. delivery of drug to a host through the skin. These elements are (1) a protective backing (2), a zone of drug containment (3), an adhesive layer for attachment to the host and, where necessary a zone of transport control, a zone of drug enhancement and a strippable release layer. It is the object of this invention to provide a method for the fabrication of transdermal drug delivery devices. It is another object of this invention to provide a method for controlling fabrication of transdermal drug delivery devices by separating the production into manipulable steps. It is a further object of this invention to provide a method for the fabrication of transdermal drug delivery devices of improved reliability. It is another object of this invention to provide a method for the modular fabrication of transdermal drug delivery devices. These and other objects of the invention will become apparent to those skilled in the art upon reading this disclosure.

BRIEF DESCRIPTION OF THE DRAWINGS

The invention will be described in further detail with reference to the accompanying drawings wherein: FIG. 1 is a schematic representation of various embodiments of incipient devices, 1a to 1n, showing some of the possible location of various elements of the devices. FIG. 9 depicts an assembled transdermal drug delivery device.

DETAILED DESCRIPTION OF THE INVENTION

Figure 1A:
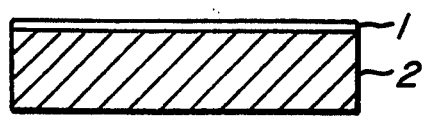
FIG. 1a represents an incipient device comprised of an protective backing 1 and layer 2 which is comprised of both a combination of both a zone of drug containment and a zone of transport enhancement.
Figure 1B:
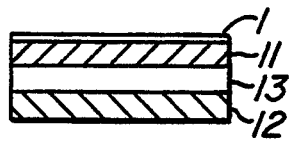
FIG. 1b represents an incipient device comprised of backing layer 1, an adjacent zone of transport enhancement 11, a zone of drug containment 13 adjacent to transport enhancement zone 11, and a second zone of transport enhancement 12, adjacent to zone of drug containment 13.
Figure 1H:
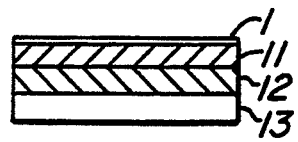
FIG. 1h represents an incipient device comprised of backing layer 1, an adjacent zone of transport enhancement 11, a second zone of transport enhancement 12 adjacent to zone of transport enhancement 11 and zone of drug containment 13 adjacent to zone of transport enhancement 12.
Figure 1C:
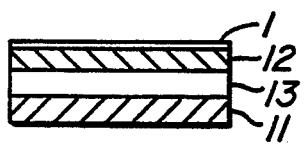
FIG. 1c represents an incipient device comprised of backing layer 1, an adjacent zone of transport enhancement 12, a zone of drug containment 13 adjacent to transport enhancement zone 12, and a second zone of transport enhancement 11, adjacent to zone of drug containment 13.
Figure 1I:
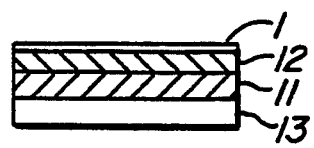
FIG. 1i represents an incipient device comprised of backing layer 1, an adjacent zone of transport enhancement 12, a second zone of transport enhancement 11 adjacent to zone of transport enhancement 12 and zone of drug containment 13 adjacent to zone of transport enhancement 11.
Figure 1D:
FIG. 1d represents an incipient device comprised of backing layer 1, an adjacent zone of drug containment 13, a zone of transport enhancement 12, adjacent to zone of drug containment 13 and a second zone of transport enhancement 11 adjacent to transport enhancement zone 12.
Figure 1J:
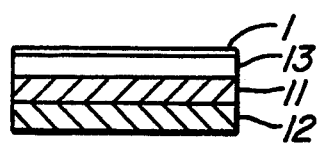
FIG. 1j represents an incipient device comprised of backing layer 1, an adjacent zone of drug containment 13, a zone of transport enhancement 11 adjacent to zone of drug containment 13 and a second zone of transport enhancement 12 adjacent to transport enhancement zone 11.
Figure 1E:
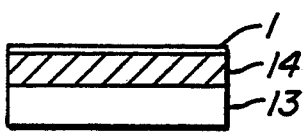
FIG. 1e represents an incipient device comprised of backing layer 1, an adjacent zone of transport enhancement 14 containing two different enhancers, a zone of drug containment 13 adjacent to transport enhancement zone 14.
Figure 1K:
FIG. 1k represents an incipient device comprised of backing layer 1, an adjacent zone of drug containment 13 and a zone of transport enhancement 14 containing two different enhancers adjacent to zone of drug containment 13.
Figure 1F:
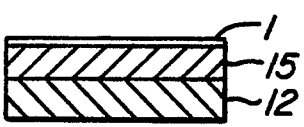
FIG. 1f represents an incipient device comprised of backing layer 1, an adjacent layer 15 containing both a zone of drug containment and a zone of transport enhancement, and a zone of transport enhancement 12, adjacent to combination layer 15.
Figure 1L:
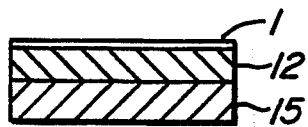
FIG. 1l represents an incipient device comprised of backing layer 1, an adjacent zone of transport enhancement 12 and a layer 15 containing both a zone of drug containment and a zone of transport enhancement adjacent to zone of transport enhancement 12.
Figure 1G:
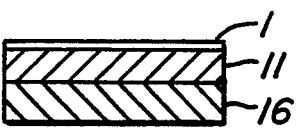
FIG. 1g represents an incipient device comprised of backing layer 1, an adjacent zone of transport enhancement 11 and a layer 16 containing both a zone of drug containment and a zone of transport enhancement adjacent to zone of transport enhancement 11.
Figure 1M:
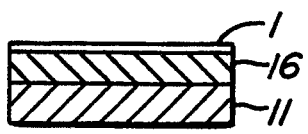
FIG. 1m represents an incipient device comprised of backing layer 1, an adjacent layer 16 containing both a zone of drug containment and a zone of transport and zone of transport enhancement 11 adjacent to layer 16.
Figure 1N:
FIG. 1n represents an incipient device comprised of backing layer 1, an adjacent layer 16 containing a zone of drug containment and a zone of transport enhancement containing two enhancers.

This invention relates to an improved method for manufacturing transdermal drug delivery devices that uses adhesive layers to accomplish the joining of the separable elements of transdermal drug delivery devices. Rather than manufacture transdermal drug delivery devices by successive application of the elements of a device by layer-by-layer build up of the device or by various forms of heat sealing, this invention describes a method whereby the various elements of the device may be fabricated separately and finally joined when need arises thus providing a heretofore unattainable degree of flexibility and reliability. To properly describe the applicability of the invention, the transdermal drug delivery device has been divided into its components or elements and the subassembly of such components and elements are hereinafter called by the terms "incipient device", "intermediary complement device" and "complement device." Since the heart of this invention is the joining those components or elements, the actual selection of the structure of these components and their location within a subassembly is left to the discretion of those skilled in the art. For example, if one skilled in the art desired to construct a device that required the presence of two transdermal permeation enhancers and a means for controlling the dosage of the drug, he could choose to separate these elements in a large number of ways. Assuming in this example, that drug transport control is obtained by the second portion of the device (complement device). The first portion (incipient device) could have the enhancers in separate layers, combined in part or in total, with the drug. FIG. 1 shows some possible configurations of incipient devices. It is important to recognize that the invention lies not in the choice of the components for the incipient device, intermediary complement device or complement device; or the location of the components in said incipient device, intermediary complement device or complement device, but in the method that combines the incipient device, intermediary complement or complement device. Permeation enhancers, for example, may be contained in a reservoir, monolithic layer, adhesive layers, or other forms and still be encompassed within the scope of this invention. Adhesives may be, but not limited to, acrylics, rubber based and silicone polymer based. By acrylic adhesives is meant polymers of various esters of acrylic or methacrylic acid, acrylamide, methacrylamide, N-alkoxyalkyl or N-alkylacrylamides. By rubber based adhesives is meant adhesives based on the various rubbers such as styrene-butadiene, polyisobutylene, polybutadiene, polyisoprene, S-I-S (polystyrene-polyisoprene-polystyrene) and S-B-S (polystyrene-polybutadiene-polystyrene) block copolymers; or on other elastomers such as polyurethane rubbers.

Protective Backing

Because of the comparatively small volume available for drug containment, the desirability of prolonged treatment from the application of a single device and the requirement for passage of substances through a structure designed to be a barrier to foreign substances, (the skin), drugs administered transdermally are usually therapeutically potent and are either aggressive solvents themselves or are contained in aggressive solvent systems. Any small loss of drug by migration through the device to its exterior during storage or use or by potentiation of its activity caused by chemical degradation, will seriously affect the dosage rate, lifetime of the device and thus, its overall utility. Unless adequate precautions are taken, sufficient drug can migrate to the surface of the device presenting an absorption hazard to the person applying the device. The protective backing is the organic equivalent of a tin can. Its purpose is to protect the contents of the device from the environment and the environment from the contents of the device. The protective backing may be variously composed. The nature of the drug contained and its enhancers, if any, dictate the characteristics of the backing. Drugs sensitive to light are contained behind opaque backings.

Where moisture absorption could cause problems, good moisture vapor barriers are chosen for backing materials. If oxygen absorption and subsequent oxidation can lead to product degradation, oxygen resistant backings are used. The specific backing used for a given application is also chosen because it acts as a protective barrier against migration of the chemicals contained in the device. Materials suitable for use as protective barriers include metal foils such as aluminum foil, polyesters such as polyethylene terephthalate, polyamides such as polycaprolactones, polyolefins such as polyethylene or polypropylene, polyacrylates such as polymethylmethacrylate or polyacrylamide, polyurethanes, vinyl polymers and copolymers such as polyvinyl chloride or polyvinylacetate, polyurethanes, cellophanes or other similar materials. Multilayer laminates may also be used. Where a single material cannot fulfill all the requirements of the backing, composite materials can be used such as metallized polyesters metallized polyvinylidene chloride, polypropylene/nylon laminates, etc. A particularly preferred backing material comprises a skin-colored polyester metal/foil laminate. In some therapies, such as wound dressings, it may be advantageous for the backing the have permeability to some compounds such as water vapor for efficacy. Such semi-permeable or permeable backings are encompassed by the term "protective backing".

Zone of Drug Containment

All transdermal devices, except placebo devices, contain chemicals to be delivered. These substances may be contained in a well defined cavity or reservoir, in a polymer matrix such as silicone rubber, in an adhesive layer or in more than one of these areas. For the purposes of this invention, the term "zone of drug containment" refers to the portion of the device containing the drug regardless of whether it is in a single location or in a number of locations. It is possible, for example, to have a transdermal drug delivery device where the drug is contained in one or more of the adhesive layers, in a monolithic structure containing microcapsules of drug and also in a drug containing reservoir all contained in the final transdermal drug delivery device. It is not a requirement of this invention that the drug be limited to one substance. Mixtures of drugs may be employed and these different drugs may be contained in different areas of the device. These combinations are included in the term "zone of drug containment." As used herein, the expression "drug" and "agent" are intended to have their broadest interpretation as to any therapeutically active substance which is delivered to a living organism to produce a desired, usually beneficial, effect. In general, this includes therapeutic agents in all of the major therapeutic areas, including, but not limited to, anti-infectives such as antibiotics and antiviral agents, analgesics and analgesic combinations, antiasthmatic agents, anticonvulsants, antidepressants, antidiabetic agents, antidiarrheals, antihistamines, anti-inflammatory agents, antimigraine preparations, antimotion sickness preparations, antinauseants, antineoplastics, antiparkinsonism drugs, antipruritics, antipsychotics, antipyretics, antispasmodics, including gastrointestinal and urinary, anticholinergics, sympathomimetrics, xanthine derivatives, cardiovascular preparations including calcium channel blockers, betablockers, antiarrythmics, antihypertensives, diuretrics, vasodilators, including general, coronary, peripheral and cerebral, central nervous system stimulants, cough and cold preparations, decongestants, diagnostics, hormones, hypnotics, immunosuppressives, muscle relaxants, parasympatholytics, parasympathomimetrics, psychostimulants, sedatives and tranquilizers.

Zone of Transport Enhancement

Because the stratum corneum layer of the skin has excellent barrier properties and resists the penetration of foreign substances, transdermal devices containing drugs that do not freely permeate the skin would require devices having large surface areas in order to deliver a therapeutically effective amount of drug. It has been discovered that certain chemicals can increase or enhance the permeability of the stratum corneum layer. Use of these enhancers has made possible the manufacture of transdermal drug delivery devices of more reasonable size. Suitable transport enhancing materials include but are not limited to, saturated aliphatic acids and derivatives such as myristic acid, isopropyl myristate, myristyl alcohol and monomyristein; unsaturated aliphatic acids and derivatives such as oleic acid, propyl oleate, oleyl alcohol and mono-olein; aryl alkyl tertiary amine derivatives including dialkyl aryl amines such as N,N-diethyl-m-toluamide; dialkyl sulfoxides such as dimethyl sulfoxide or decyl methyl sulfoxide; 1-substituted azacycloalkan-2-ones such as 1-dodecylazacycloheptan-2-one; dialkyl amides such as dimethyl or diethylacetoamide and thiogylcolates such as calcium thioglycolate. In some cases, two or more enhancers are used when the degree of permeation enhancement of the combination is greater than the sum of the enhancers alone; for example, mixtures of isopropyl myristate and N,N,-diethyl-m-toluamide have been used to good effect. Enhancers, like drugs, may be located at one or more different physical locations. Regardless of whether they are combined in the zone of drug containment or found in another location and are included in the term "zone of transport enhancement." Skin permeability may also be modified by the use of other a agents such as enzyme inhibitors e.g. acetylcholine esterase inhibitors, hydrocortisone and the like and are encompassed by the term "enhancer". Thus, single layer may contain permeation enhancers and drug and be denoted as a zone of both drug containment and zone of transport enhancement.

Zone of Transport Control

It is important that the amount of drug delivered to the host and absorbed transdermally by the host's system be maintained at therapeutically useful levels for prolonged periods. Polymeric membrane materials may be used to govern the amount of drug released from a transdermal device, over time, by controlling the flux of drug directly or by controlling the flux of enhancers. The membrane can be selected to deliver drug at the desired rate. The use of a membrane that reliably delivers drug at flux higher than can be transported through the skin than can be the skin relies upon the skin for transport control, and yields the smallest possible device size. Delivery rate controlling membranes assure the constant maintenance of a controlled delivery rate from the early stages of the drug administration period to beyond a 24 hour period. Moreover, in the case of extremely permeable skin or highly permeable drugs, the rate controlling membrane has the functions as a safety mechanism that constrains the delivery of drug to mammalian skin to that level useful of therapy but below the toxic limit. Representative polymers for rate controlling membranes include polyolefins such as polyethylene and polypropylene, polyamides, polyesters, ethylene-methacrylate copolymers, segmented copolymers of butylene terephthalate 33% and tetramethylene ether terephthalate 67%, segmented copolymer of proplylene terephthalate 58% and polytetramethylene ether terephthalate 42%, block copolymers of tetramethylene terephthalate-polytetramethylene ether glycol terephthalate, ethylene-vinyl acetate copolymers, ethlyene-vinyl methylacetate copolymers, ethylene-vinyl ethylacetate copolymers, ethylene-vinyl propylacetate copolymers. polyisoprene, polyacrylonitrile, ethylene-propylene copolymers, and the like. Although it is more common to control delivery of the drug to the body by moderating its delivery to the skin with a zone of transport control; other systems, in which the zone of transport control is used to moderate the rate of delivery of skin permeation enhancer have been used. In these systems, the rate of delivery of enhancer to the skin is controlled. This changes the permeability of the skin allowing drug to permeate the skin and enter the body at a useful rate. Thus, by adjusting the rate of delivery of the enhancer the rate of drug delivery is also controlled. The term "zone of transport control" can therefore refer to control of the drug, one or more enhancers or both drug and enhancers.

Incipient Device

An incipient device, for the purposes of this invention, is defined as a transdermal drug delivery device that lack one or more elements required to form a complete and fully functioning transdermal drug delivery device. An incipient device may, for example, contain a protective backing, a zone of drug enhancement, zone of drug containment but lacks the required zone of drug transport control and a zone of transport enhancement appropriate for the intended use. In another embodiment, the incipient device may be composed of an protective backing, a zone of drug transport enhancement, a zone of transport control but not contain the required zone of drug containment. The missing elements are supplied by a complement device or a complement device in concert with an intermediary complement device.

Complement Device

Figure 2A:
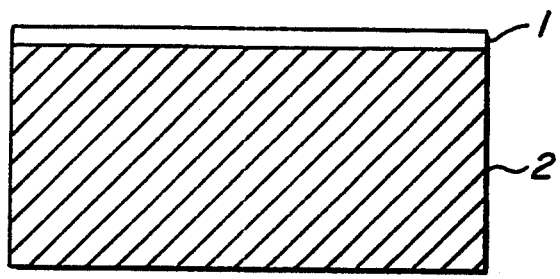
FIGS. 2a, 2b, 3a, 3b, 4a, 4b, 4c, 5a, 5c, 6a, 6b, 6c, 7a, 7b, 7c, 9, 10a, 10b and 10c are schematic representations of some embodiments of incipient and complement devices.
Figure 2B:
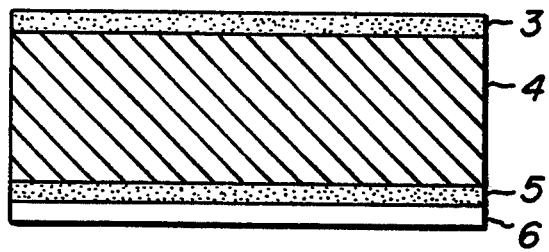
Figure 3A:
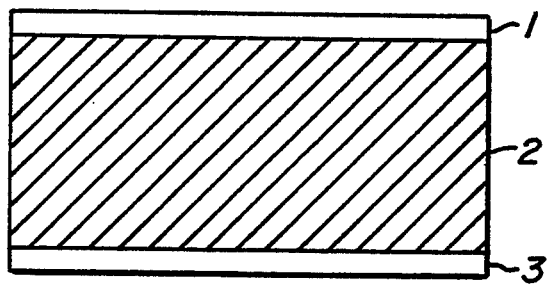
Figure 3B:
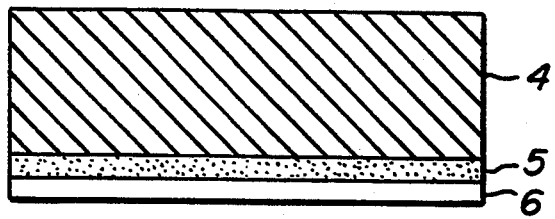

A complement device is a structure that alone or in combination with an intermediary complement device, if present at all, provides the elements missing from the corresponding incipient device that are required for a fully efficacious transdermal drug delivery system. For example, the incipient device may contain all the elements for efficacious drug delivery except a zone of drug containment. The complement device, in this case, would contain the missing zone of drug containment. An example of such combination is illustrated in FIG. 2 where incipient device 2a is comprised of protective backing 1; zone of transport enhancement and zone of transport control 2. Complement device 2b is comprised of adhesive layers 3 and 5, support layer 4 and removable release liner 6. The required zone of drug containment could be contained in one or both of the adhesive layers or support layer without deviating from the scope of this invention. Selection of the mode of providing drug containment is within the discretion of those skilled in the art of device design. The complement device will be comprised in the minimum embodiment, of a material coated with an adhesive on one side, whose main function is to add an adhesive interface for the eventual attachment of the transdermal drug delivery device to the host. Such a system is illustrated in FIG. 3, where, complement device 3b is comprised of adhesive layer 5, support layer 4 and removable release liner 6. In this embodiment, the support layer, 4 would have little, if any, effect upon the rate of transfer of material from the total device to the host.

Intermediary Complement Device

Figure 4A:
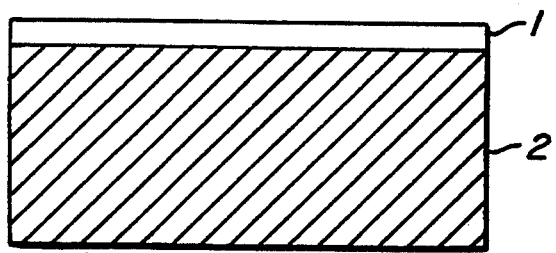
Figure 4B:
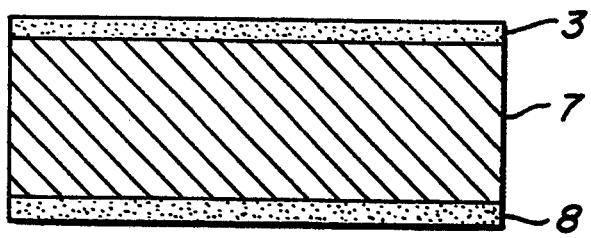
Figure 4C:
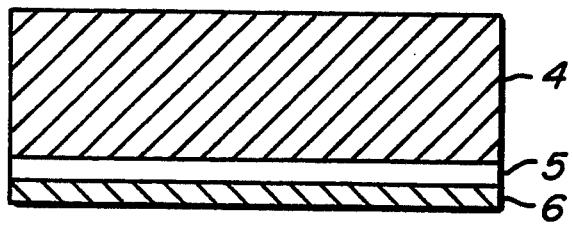

The intermediary complement device is a separate and distinct structure whose main function is to join the incipient device to the complement device. The intermediary complement device may, in some embodiments, supply some but not all of the elements missing in the incipient device that are required by the complement device in order to supply the elements lacking in the incipient device. For example, the incipient device may require a zone of transport control and a zone of drug containment in order to be efficacious. The zone of drug containment could be located in the complement device and the zone of transport control could be located in the intermediary complement device. It is the combination of intermediary complement device and complement device that provides all the missing elements of the incipient device. FIG. 4 illustrates an embodiment where intermediary complement device 4b is comprised of adhesive layers 3 and 8 and support layer 7. In this embodiment, the double-sided adhesive tape would be constructed so as to offer little, if any, impediment to the transfer of material through its bulk.

By following the directions of this invention, for example, one of ordinary skill in the art could produce a quantity of drug containing incipient devices in a single production operation. At a different time, a number of complement devices and intermediate complementary devices having different compositions and differing characteristics may be produced in anticipation of future assembly. Since the components of the final device may be tested for quality assurance as individual units of the finished article, they may be later combined in the most advantageous way. If, for example, upon later analysis, part of a production run of manufactured complement device, wherein the drug is contained in a polymeric matrix, was found to have a higher than designed drug concentration which would lead to a desirably high drug flux, one could then choose to combine it with a complement device that has a zone of transport control characterized by a drug flux lower than the original design flux but now appropriate for the incipient device. In a similar manner, off-the-shelf modules may be assembled for a large variety of drug therapies after their key characteristics are determined.

BRIEF DESCRIPTION OF THE DRAWINGS

FIG. 1 presents a number of possible embodiments of the claimed invention illustrating variation in placement of the components of incipient devices.

FIG. 2 illustrates one embodiment of the claimed invention wherein the resultant transdermal patch are formed by combination of two layered structures, the adhesive layers used to join the parts is contained as part of the complement device.

FIG. 3 illustrates one embodiment of the claimed invention wherein the resultant transdermal patch is formed by combination of two layered structures, the adhesive layers used to join the parts are contained as part of the incipient device.

FIG. 4 illustrates one embodiment of the claimed invention where the patch is formed by combination of three layered structures, the adhesive layers used to join the parts are all contained in one of the structures.

Figure 5A:
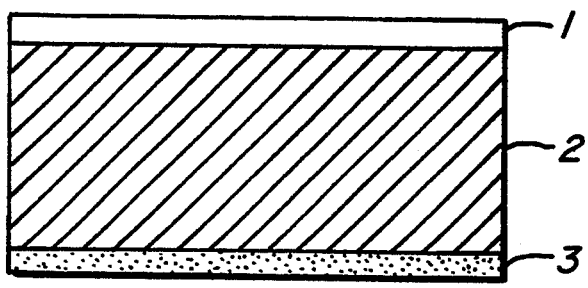
Figure 5B:
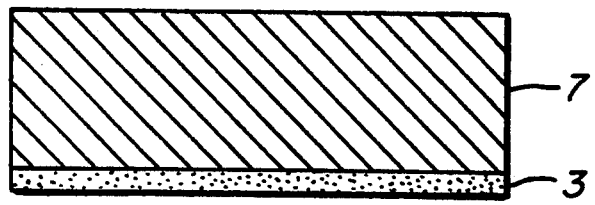
Figure 5C:
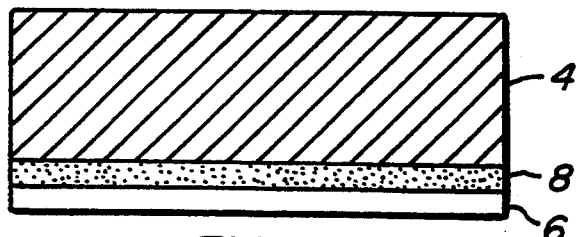

FIG. 5 illustrates one embodiment of the claimed invention wherein the patch is formed by combination of three layered structures, the adhesive layers used to join the parts are contained in separate structures.

Figure 6A:
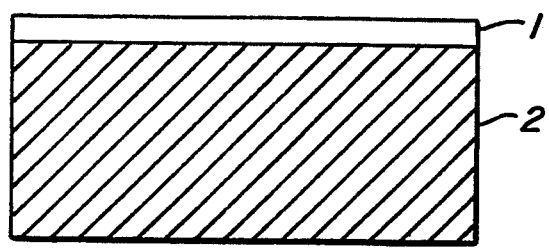
Figure 6B:
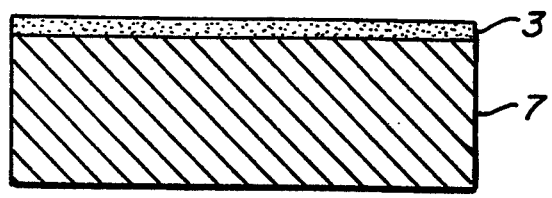
Figure 6C:
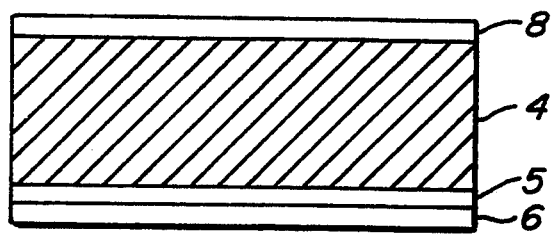

FIG. 6 illustrates one embodiment of the claimed invention wherein the patch is formed by combination of three layered structures, the adhesive layers used to join the parts are contained in separate structures different that those shown in FIG. 5.

Figure 7A:
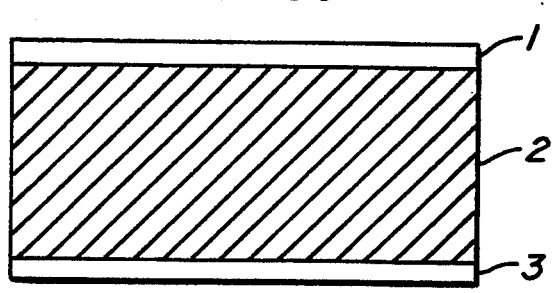
Figure 7B:
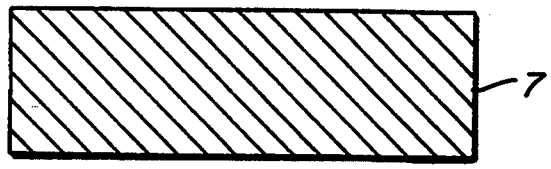
Figure 7C:
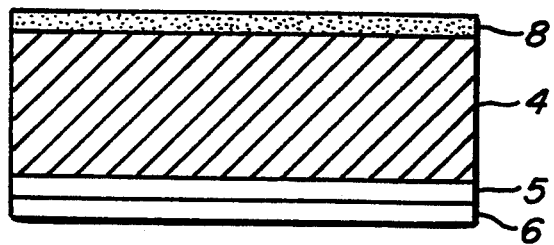

FIG. 7 illustrates one embodiment of the claimed invention wherein the patch is formed by combination of three layered structures, the adhesive layers used to join the parts are contained in separate structures different that those shown in FIGS. 5 or 6.

Figure 8:
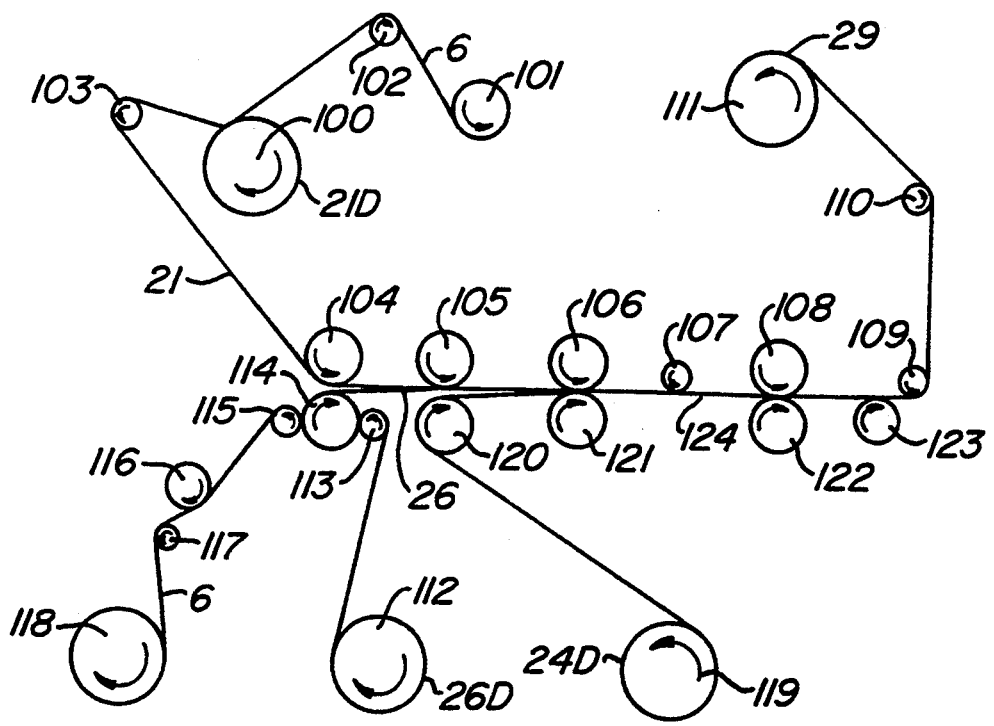
FIG. 8 illustrates a generalized apparatus for combining incipient devices with intermediary complement and complement devices.

FIG. 8 illustrates one possible configuration of equipment suitable for assembling transdermal devices according to the herein described invention.

Figure 9:
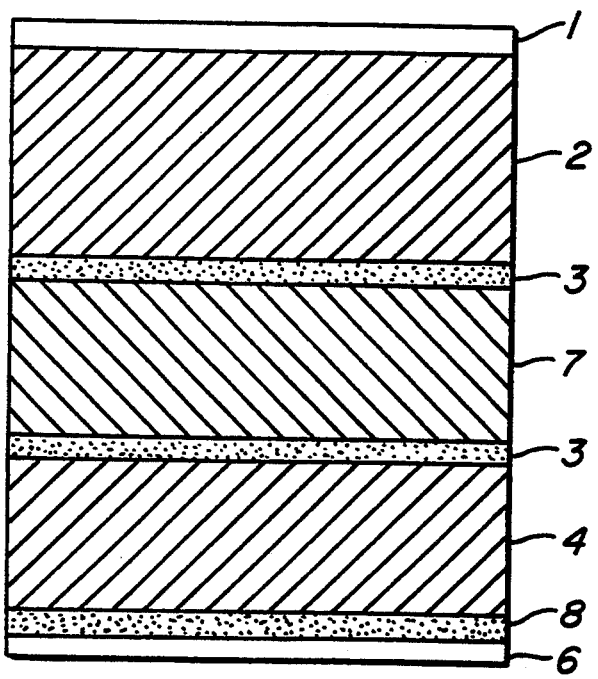

FIG. 9 illustrates that the same composition of a transdermal device would result from joining the layered structures shown in FIGS. 4, 5, 6 or 7.

Figure 10A:
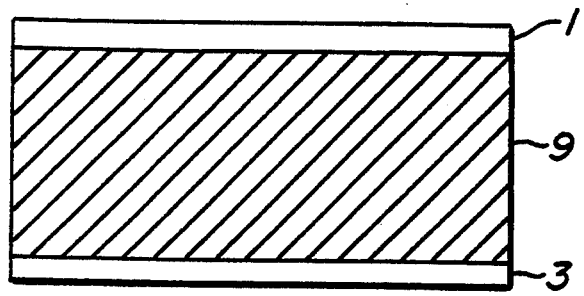
Figure 10B:
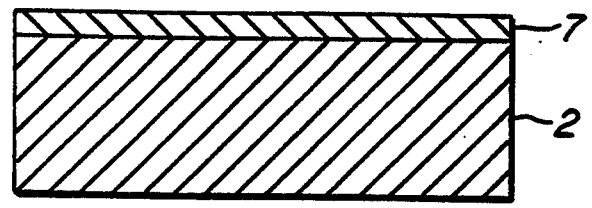
Figure 10C:

FIG. 10 illustrates one embodiment of the claimed invention wherein the resultant transdermal patch is formed by combination of three layered structures, the adhesive layers used to join the parts are contained in one of the structures.

Referring more specifically now to the drawings, FIG. 1 illustrates a number of incipient devices.

This FIG. 1 shows the generic form of the incipient device, comprised of a protective backing 1 and a combined zone of transport enhancement and zone of drug containment, 2. FIG. 1b to 1n illustrate possible configurations of incipient device 1a wherein two transport enhancers are used and where in FIG. 1b, 1c, 1d, 1h, 1i and 1j, one enhancer is contained in strata 11; the other enhancer is contained in strata 12 and the drug is contained in strata 13. In FIG. 1e and 1k, both enhancers are contained in strata, 14. In FIG. 1f and 1l, one of the enhancers is combined with the drug in strata 15. In FIGS. 1g and 1m, the other enhancer is combined with the drug in strata 16. In FIG. 1n, the enhancers and drug are all combined together in strata 17. For the purposes of this invention, the structures in FIG. 1b to 1n are all encompassed in the structure 1a. One of ordinary skill in the art can envision a large number of variations in the structure of the incipient device, complement device or both that may be combined in the manner described in this invention without deviating from this invention. If, in order for completion, an incipient device, such as shown in embodiment 1a, required a zone of drug transport control, the required complement device may take many forms, such as shown in FIG. 2 or in conjunction with an intermediary complement device such as shown in FIG. 4. In FIG. 2, incipient device 2a has the generic form shown in FIG. 1a and thus could have any of the specific forms 1b through 1n. In FIG. 2, complementary device 2b is comprised of adhesive layer 3, adhesive layer 5, support layer 4 and removable release liner 6. In FIG. 4, complementary device 4c is comprised of adhesive layer 5, support film 4 and removable liner 6. Intermediary complementary device 4b is comprised of zone of transport control 7, adhesive layer 3 and removable release liner 6. The following examples further illustrate the invention. These examples are not intended to limit the invention in any manner.

EXAMPLE 1

A solution of nicotine containing Dow Pellethane ® 2363-80AE polyurethane, is made by mixing Pellethane ® pellets into tetrahydrofuran in a container; adding 10 wt °/$_{oo}$ liquid nicotine free base, and then agitating the mixture on a bottle roller for three days. A 3M Corporation polyester medical film, Scotchpak ® 1022 is coated with the nicotine-Pellethane ® solution and the tetrahydrofuran solvent continuously removed by passing the coated film through a heated oven. The coated backing taken up on a roll with a removable release liner for ease of handling and designated release-lined Incipient Device A. At a later date, the nicotine containing, Incipient Device A is unrolled, liner removed and contacted with a complement device commercially available as doubly-adhesive coated polyethylene film, 3M Corporation 3M-1109. The resultant nicotine releasing device corresponds to the system illustrated in FIG. 2 where Incipient Device A corresponds to incipient device 2a and the double-sided tape corresponds to complement device 2b. In this example, the zone of drug containment is zonal area 2, zone of transport control is in support layer 4. Double-sided tape 3M-1109 supplied 3M Corporation is available with a removable release liner which remains as part of the device as layer 6.

EXAMPLE 2

Chlorpheniramine containing incipient device and isopropyl myristate containing complement devices are prepared in the following illustrative example. A solution of chlorpheniramine containing Dow Pellethane ® 2363-80AE polyurethane, is made by mixing Pellethane ® pellets into tetrahydrofuran in a container, adding 30 wt °/$_{oo}$ chlorpheniramine free base, and then agitating the mixture on a bottle roller for three days. A 3M Corporation polyester medical film, Scotchpak ® 1109 is coated with the chlorpheniramine-Pellethane ® solution and the tetrahydrofuran solvent continuously removed by passing the coated film through a heated oven. A solution of pressure sensitive adhesive Dow Bio PSA ® grade X7-2920 adhesive is applied to the chlorpheniramine containing Dow Pellethane ® coated backing and the solvent continuously removed by passing the film through a heated oven and is then taken up on a roll with a removable release liner for ease of handling and designated Incipient Device B. In a separate operation, ATOCHEM, Polyether Block Amide film, Pebax ® film 4033-SN-00 is coated with a solution of Dow Bio PSA ® Adhesive X7-2920 containing 20 wt °/$_{oo}$ isopropyl myristate, dried, laminated and rolled up with a removable release liner and designated release-lined Complement Device B. At a later date, the chlorpheniramine containing, Incipient Device B is unrolled, liner removed and contacted with Complement Device B. The resultant chlorpheniramine releasing device corresponds to the system illustrated in FIG. 3 where Incipient Device B corresponds to incipient device 3a and Complement Device B corresponds to complement device 3b. In this example, the zone of drug containment is zonal area 2, zone of transport control is in support layer 4 and zone of transport enhancement is in adhesive layer 5.

EXAMPLE 3

Pressure sensitive adhesive Dow Bio PSA ® is coated upon both sides of a fibrous paper to produce Intermediary Complement Device C and taken up in the form of rolled film with a removable release liner for ease of unrolling. Incipient Device A from Example 1 (liner removed) and Complement Device B from Example 2 are joined together by means of Intermediary Complement Device C (liner removed). This assembly is depicted in FIG. 4 where Incipient Device A corresponds to incipient device 4a, Intermediary Complement Device C corresponds to complement device 4b and Complement Device B corresponds to complement device 4c. In this example, the zone of drug containment is zonal area 2, zone of transport control is in layer support layer 4, zone of transport enhancement is in adhesive layer 5 and the fibrous support 7 is doubly coated with adhesive layers 3 and 8.

EXAMPLE 4

A solution of physostigmine containing Dow Pellethane ® 2363-80AE polyurethane, is made by mixing Pellethane ® pellets into tetrahydrofuran in a container, adding 30 wt $°/_{oo}$ physostigmine free base, and then agitating the mixture on a bottle roller for three days. A 3M Corporation polyester medical film, Scotchpak ® 1109 is coated with the physostigmine-Pellethane ® solution and the tetrahydrofuran solvent continuously removed by passing the coated film through a heated oven. Similarly, a solution of pressure sensitive adhesive, Dow Bio PSA ®, grade X7-2920, containing glycerol monooleate is applied to the physostigmine/Pellethane ® coated backing. The solvent is continuously removed by passing the film through a heated oven and is then taken up on a roll with a removable release liner and designated Incipient Device D. In a separate operation, fibrous paper sheet impregnated with clonidine is coated with a solution of Dow Bio PSA ® Adhesive X7-2920 containing 20 wt $°/_{oo}$ isopropyl myristate, dried and rolled up with a removable release liner and designated release-lined Complement Device B. In another separate operation, ATOCHEM, Polyether Block Amide film, Pebax ® film, 4033-SN-00, manufactured by Du Pont of Canada, is coated with a solution of Dow Bio PSA ® Adhesive X7-2920 containing 20 wt $°/_{oo}$ isopropyl myristate, dried and rolled up with a removable release liner and designated release-lined Complement Device D. At a later date, the physostigmine containing, Incipient Device D is contacted with Intermediary Complement Device D (liner removed) and Complement Device D. The resultant physostigmine and clonidine releasing device corresponds to the system illustrated in FIG. 5 where Incipient Device D corresponds to incipient device 5a, Intermediary Complement Device D, corresponds to intermediary complement device 5b and Complement Device D corresponds to complement device 5c. In this example, the zones of chug containment are zonal areas 2 and 7, zone of transport control is in layer 4 and zones of transport enhancement are in adhesive layers 3 and 8.

EXAMPLE 5

A solution of fentanyl containing Dow Pellethane ® 2363-80AE polyurethane, is made by mixing Pellethane ® pellets into tetrahydrofuran in a container, adding 30 wt $°/_{oo}$ fentanyl, and then agitating the mixture on a bottle roller for three days. 3M Corporation polyester medical film, Scotchpak ® 1109 is coated with the fentanyl Pellethane ® solution. The tetrahydrofuran solvent is then continuously removed by passing the film through a heated oven and is then taken up on a roll with a removable release liner and designated release-lined, Incipient Device E. A solution of pressure sensitive adhesive Dow Bio PSA ® grade X7-2920 adhesive containing glycerol monooleate is applied to Pebax ® film 5533-SA-00, solvent is removed and the coated film is taken up in roll form with a release liner and designated release-lined Intermediary Complement Device E. In a separate step, fibrous paper sheet impregnated with an isopropanol gel is coated with pressure sensitive adhesive Dow Bio PSA ® grade X7-2920 adhesive on the both sides and the coated film taken up in roll form with a removable release liner and designated release-lined Complement Device E. At a later date, Incipient Device E (liner removed) and Complement Device E are joined by means of Intermediary Complement Device E (liner removed). The resultant fentanyl releasing device corresponds to the system illustrated in FIG. 6 where Incipient Device D corresponds to incipient device 6a, Intermediary Complement Device D, corresponds to intermediary complement device 6b and Complement Device D corresponds to complement device 6c. In this example, the zone of drug containment is zone/area 2, zone of transport control is in layer 7 and zones of transport enhancement are in adhesive layer 3 and support layer 4.

EXAMPLE 6

Incipient Device B from Example 2 (liner removed) and Complement Device E from Example 5 are joined by means of Pebax ® film 5533-SA-00, Intermediary Device F. The resultant chlorpheniramine releasing device corresponds to the system illustrated in FIG. 7 where Incipient Device B corresponds to incipient device 7a, Intermediary Complement Device F, corresponds to intermediary complement device 7b and complement Device E corresponds to complement device 7c. In this example, the zone of drug containment is zonal area 2, zone of transport control is in layer 7 and zone of transport enhancement is in adhesive layer 8.

EXAMPLE 7

A solution of nicotine-loaded Pellathane 2363-80AE was made by mixing Pellethane pellets into tetrahydrofuran, adding 10 wt $°/_{oo}$ liquid nicotine, and agitating on a bottle roller for three days. A layer of backing material grade 3M-1005 was spread in a petri dish and covered with the matrix mixture. The petri dish was covered, and the matrix was left for the solvent to evaporate at room temperature. The monolith was contacted with polyethylene, double-sided, medical adhesive tape grade 3M-1109. The resultant nicotine releasing device corresponds to the system illustrated in FIG. 2 where the incipient device herein corresponds to incipient device 2a and the double-sided tape corresponds to complement device 2b. In this example, the zone of drug containment is zonal area 2, zone of transport control is in support layer 4. Double-sided tape 3M-1109 supplied 3M Corporation is available with a removable release liner which remains as part of the device as layer 6.

EXAMPLE 8

A solution of nicotine-loaded Pellathane 2363-80AE was made by mixing Pellethane pellets into tetrahydrofuran, adding 10 wt $^o/_{oo}$ liquid nicotine, and agitating on a bottle roller for three days. A layer of backing material grade 3M-1005 was spread in a petri dish and covered with the matrix mixture. The petri dish was covered, and the matrix was left for the solvent to evaporate at room temperature. The monolith was coated with polyethylene, double-sided, adhesive tape grade 3M-1512. The resultant nicotine releasing device corresponds to the system illustrated in FIG. 2 where the incipient device herein corresponds to incipient device 2a and the double-sided tape corresponds to complement device 2b. In this example, the zone of drug containment is zonal area 2, zone of transport control is in support layer 4. Double-sided tape 3M-1109 supplied 3M Corporation is available with a removable release liner which remains as part of the device as layer 6.

Various mechanical appliances and contrivances may be used to join the incipient devices with intermediary complement and complement devices. FIG. 8 depicts one such arrangement where the release liner 6 is removed from release-lined incipient device 21D on supply roll 100 by passing the separated liner over idler roller 102 and is taken up on roll 101. Incipient device 21 with liner removed is passed over idler roller 103, between roller pairs 104 and 114; 105 and 120. Incipient device 21 is joined with intermediary complement device 26 and release-lined complement device 24D, under paired rollers 106 and 121. Release liner 6 is removed from release-lined intermediary complement device 26D, originating from roll 112 by passing release-lined intermediary complement device 26D over roller 113, separating the release liner 6 between roller 114 and roller 115. The removed liner is passed by idler rollers 116 and 117 and taken up on drum 118. Release-lined intermediary complement device 26D is passed over roll 114 where it is joined with incipient device 21, and complement device 24D under paired rollers 106 and 121. Release-lined complement device 24D is removed from supply roll 119; passed over roll 120 and joined with incipient device 26D and intermediary complement device D under paired rollers 106 and 121. The now combined layers, (transdermal device 29), is passed under roller 107; between roller pair 108 and 122; over roller 123; under roll 109; over idler roller 110 and taken up on roll 111. Assembled transdermal delivery device 29 is depicted in FIG. 9 where the zones of drug containment are zonal areas 2 and 7, zone of transport control is in layer 4 and zones of transport enhancement are in adhesive layers 3 and 8, protective layer is 1 and removable release liner is 6. It is within the skill of those familiar in the mechanical arts to add various additional stages to the described apparatus, such as patch cutting rolls, without deviating from the scope of this invention.

EXAMPLE 9

A gel of 50% Ethanol (Enhancer 1) in hydroxypropyl cellulose is applied to a medical grade protective backing material 3M-1005 film. In a subsequent step, the gel surface is contacted with the adhesive face of a release-lined tape and taken up in roll form. This protective backing/ethanol-water gel/adhesive/release-lined assembly is designated release-lined Incipient Device F. The transport controlling membrane in this example is fabricated from ethylene/vinyl acetate (EVA) copolymer of the type described in U.S. Pat. 4,144,317 with vinylacetate content of about 40% (EVA 40). A layer of 10% nitroglycerin in Pellethane on EVA 40 is prepared according to the method described in Example 1, taken up with a release liner and designated release-lined Intermediary Complement Device F. In a separate step, a solution of 5% isopropyl myristate (Enhancer 2) in Dow Bio PSA® grade X7-2920 adhesive is coated upon a release liner and designated release-lined Complement Device F. At a later date, Incipient Device F (liner removed) and Complement Device F are joined by means of Intermediary Complement Device F (liner removed). The resultant nitroglycerin releasing device corresponds to the system illustrated in FIG. 10 where Incipient Device F corresponds to incipient device 10a, Intermediary Complement Device F, corresponds to intermediary complement device 10b and Complement Device F corresponds to complement device 10c. In this example, protective backing is layer 1, release liner is layer 6, the zone of drug containment is zonal area 2, zone of transport control is in layer 7 and zones of transport enhancement are in adhesive layer 5 and layer 9.

It will be apparent to those skilled in this art that modifications may be made to the embodiments or changes may made to the embodiments as herein described which will come within the spirit of the invention and within purview and scope of the appended claims.

I claim:
1. A method for the fabrication of transdermal delivery devices comprising:
 a) joining by an adhesive means, the surface most distal to the protective backing of an incipient device to,
 b) the surface most distal from the release layer of a complement device, where said complement device is comprised of at least one layer in addition to a release liner and
 c) recovering said transdermal device.
2. A method according to claim 1 where said incipient device is comprised of:
 a) an protective backing layer,
 b) a zone of drug containment,
 c) a zone of transport enhancement,
 d) a zone of transport control, and
said complement device is comprised of:
 e) an adhesive layer,
 f) a support layer,
 g) a second adhesive layer,
 h) a removable release liner, and
 i) recovering said device.
3. A method according to claim 1 where said incipient device is comprised of:
 a) an protective backing layer,
 b) a zone of drug containment,
 c) a zone of transport control, and
said complement device is comprised of:
 d) an adhesive layer,
 e) a support layer,
 f) a second adhesive,
 g) a zone of transport enhancement,
 h) a removable release liner, and
 i) recovering said device.
4. A method according to claim 1 where said incipient device is comprised of:
 a) an protective backing layer,
 b) a zone of drug containment,
 c) a zone of transport enhancement, and
said complement device is comprised of:
 d) an adhesive layer,
 e) a support layer, f) a second adhesive layer,
g) a zone of transport control,
h) a removable release liner, and
i) recovering said device.

5. A method according to claim 1 where said incipient device is comprised of:
a) an protective backing layer,
b) a zone of drug containment, and said complement device is comprised of:
c) an adhesive layer,
d) a support layer,
e) a zone of transport enhancement,
f) a zone of transport control,
g) a second adhesive layer, and
h) a removable release liner,
i) recovering said device.

6. A method according to claim 1 where said incipient device is comprised of:
a) an protective backing layer,
b) a zone of drug containment,
c) a zone of transport control, and
said complement device is comprised of:
d) an adhesive layer,
e) a support layer,
f) a second adhesive layer,
g) a removable release liner, and
h) recovering said device.

7. A method according to claim 1 where said incipient device is comprised of:
a) an protective backing layer,
b) a zone of drug containment, and said complement device is comprised of:
c) an adhesive layer,
d) a zone of transport control,
e) a support layer,
f) a second adhesive layer,
g) a removable release liner, and
h) recovering said device.

8. A method according to claim 1 where said incipient device is comprised of:
a) an protective backing layer,
b) a zone of drug containment.
c) a zone of transport enhancement, and
said complement device is comprised of:
d) an adhesive layer,
e) a support layer,
f) a second adhesive layer,
g) a removable release liner, and
h) recovering said device.

9. A method according to claim 1 where said incipient device is comprised of:
a) an protective backing layer,
b) a zone of drug containment, and
said complement device is comprised of:
c) an adhesive layer,
d) a zone of transport enhancement,
e) a support layer,
f) a second adhesive layer,
g) a removable release liner, and
h) recovering said device.

10. A method according to claim 1 where said incipient device is comprised of:
a) an protective backing layer
b) a zone of drug containment, and
said complement device is comprised of:
c) an adhesive layer,
d) a support layer,
e) a second adhesive layer,
f) a removable release liner, and
g) recovering said device.

11. A method according to claim 1 where said incipient device is comprised of:
a) an protective backing layer,
b) a zone of transport enhancement,
c) a zone of transport control, and
said complement device is comprised of:
d) an adhesive layer,
e) a support layer,
f) a zone of drug containment,
g) a second adhesive layer,
h) a removable release liner, and
i) recovering said device.

12. A method according to claim 1 where said incipient device is comprised of:
a) an protective backing layer,
b) a zone of transport enhancement, and
said complement device is comprised of:
c) an adhesive layer,
d) a support layer,
e) a zone of transport control,
f) a zone of drug containment,
g) a second adhesive layer,
h) a removable release liner, and
i) recovering said device.

13. A method according to claim 1 where said incipient device is comprised of:
a) an protective backing layer,
b) a zone of transport enhancement, and
said complement device is comprised of:
c) an adhesive layer,
d) a support layer,
e) a zone of drug containment,
f) a second adhesive layer,
g) a removable release liner, and
h) recovering said device.

14. A method according to claim 1 where said incipient device is comprised of:
a) an protective backing layer,
b) a zone of transport control, and
said complement device is comprised of:
c) an adhesive layer,
d) a support layer,
e) a zone of transport enhancement, and
f) a zone of drug containment,
g) a second adhesive layer,
h) a removable release liner, and
i) recovering said device.

15. A method according to claim 1 where said incipient device is comprised of:
a) an protective backing layer,
b) a zone of transport control, and
said complement device is comprised of:
c) an adhesive layer,
d) a support layer,
e) a zone of drug containment,
f) a second adhesive layer,
g) a removable release liner, and
h) recovering said device.

16. A method according to claim 1 where said incipient device is comprised of:
a) an protective backing layer,
b) a zone of drug containment,
c) a zone of transport enhancement,
d) a zone of transport control,
e) an adhesive layer, and
said complement device is comprised of:

f) a support layer,
g) a second adhesive layer,
h) a removable release liner, and
i) recovering said device.

17. A method according to claim 1 where said incipient device is comprised of:
a) an protective backing layer,
b) a zone of drug containment,
c) a zone of transport control,
d) an adhesive layer, and
said complement device is comprised of:
e) a support layer,
f) a second adhesive,
g) a zone of transport enhancement,
h) a removable release liner, and
i) recovering said device.

18. A method according to claim 1 where said incipient device is comprised of:
a) an protective backing layer,
b) a zone of drug containment,
c) a zone of transport enhancement,
d) an adhesive layer, and
said complement device is comprised of:
e) a support layer,
f) a second adhesive layer,
g) a zone of transport control,
h) a removable release liner, and
i) recovering said device.

19. A method according to claim 1 where said incipient device is comprised of:
a) an protective backing layer,
b) a zone of drug containment,
c) an adhesive layer, and
said complement device is comprised of:
d) a support layer,
e) a zone of transport enhancement,
f) a zone of transport control,
g) a second adhesive layer, and
h) a removable release liner,
i) recovering said device.

20. A method according to claim 1 where said incipient device is comprised of:
a) an protective backing layer,
b) a zone of drug containment,
c) a zone of transport control,
d) an adhesive layer, and
said complement device is comprised of:
e) a support layer,
f) a second adhesive layer,
g) a removable release liner, and
h) recovering said device.

21. A method according to claim 1 where said incipient device is comprised of:
a) an protective backing layer,
b) a zone of drug containment,
c) an adhesive layer, and
said complement device is comprised of:
d) a zone of transport control,
e) a support layer,
f) a second adhesive layer,
g) a removable release liner, and
h) recovering said device.

22. A method according to claim 1 where said incipient device is comprised of:
a) an protective backing layer,
b) a zone of drug containment,
c) a zone of transport enhancement,
d) an adhesive layer, and
said complement device is comprised of:
e) a support layer,
f) a second adhesive layer,
g) a removable release liner, and
h) recovering said device.

23. A method according to claim 1 where said incipient device is comprised of:
a) an protective backing layer,
b) a zone of drug containment,
c) an adhesive layer, and
said complement device is comprised of:
d) a zone of transport enhancement,
e) a support layer,
f) a second adhesive layer,
g) a removable release liner, and
h) recovering said device.

24. A method according to claim 1 where said incipient device is comprised of:
a) an protective backing layer
b) a zone of drug containment,
c) an adhesive layer, and
said complement device is comprised of:
d) a support layer,
e) a second adhesive layer,
f) a removable release liner, and
g) recovering said device.

25. A method according to claim 1 where said incipient device is comprised of:
a) an protective backing layer,
b) a zone of transport enhancement,
c) a zone of transport control,
d) an adhesive layer, and
said complement device is comprised of:
e) a support layer,
f) a zone of drug containment,
g) a second adhesive layer,
h) a removable release liner, and
i) recovering said device.

26. A method according to claim 1 where said incipient device is comprised of:
a) an protective backing layer,
b) a zone of transport enhancement,
c) an adhesive layer, and
said complement device is comprised of:
d) a support layer,
e) a zone of transport control,
f) a zone of drug containment,
g) a second adhesive layer,
h) a removable release liner, and
i) recovering said device.

27. A method according to claim 1 where said incipient device is comprised of:
a) an protective backing layer,
b) a zone of transport enhancement,
c) an adhesive layer, and
said complement device is comprised of:
d) a support layer,
e) a zone of drug containment,
f) a second adhesive layer,
g) a removable release liner, and
h) recovering said device.

28. A method according to claim 1 where said incipient device is comprised of:
a) an protective backing layer,
b) a zone of transport control,
c) an adhesive layer, and
said complement device is comprised of:
d) a support layer, e) a zone of transport enhancement, and
f) a zone of drug containment,
g) a second adhesive layer,
h) a removable release liner, and
i) recovering said device.

29. A method according to claim 1 where said incipient device is comprised of:
a) an protective backing layer,
b) a zone of transport control,
c) an adhesive layer, and
said complement device is comprised of:
d) a support layer,
e) a zone of drug containment,
f) a second adhesive layer,
g) a removable release liner, and
h) recovering said device.

30. A method according to claim 1 where said drug is nicotine.

* * * * *